US005935841A

United States Patent [19]

Trinci et al.

[11] Patent Number: 5,935,841

[45] **Date of Patent: *Aug. 10, 1999**

[54] MICROBIOLOGICAL PROCESS

[75] Inventors: Anthony Peter Joseph Trinci, Stockport; Geoffrey David Robson, Manchester; Marilyn Gail Wiebe, Stockport; Thomas William Naylor, Newton Aycliffe; Trevor Williamson, Seaham, all of United Kingdom

[73] Assignee: Zeneca Limited, London, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/687,571

[22] PCT Filed: Feb. 10, 1995

[86] PCT No.: PCT/GB95/00273

§ 371 Date: Aug. 9, 1996

§ 102(e) Date: Aug. 9, 1996

[87] PCT Pub. No.: WO95/21910

PCT Pub. Date: Aug. 17, 1995

[30] Foreign Application Priority Data

Feb. 10, 1994 [GB] United Kingdom .................. 9402604

[51] Int. Cl.[6] .............................. C12N 1/00; C12N 1/02; C12N 1/14; A23C 9/12

[52] U.S. Cl. .................................... 435/254.1; 435/254.7; 435/261; 435/911; 426/61; 426/665; 424/93.3; 424/93.5

[58] Field of Search ............................ 435/254.1, 254.7, 435/261, 911; 424/93.3, 93.5; 426/61, 665

[56] References Cited

FOREIGN PATENT DOCUMENTS

| | | |
|---|---|---|
| 123 434 | 10/1984 | European Pat. Off. . |
| 91 17669 | 11/1991 | WIPO . |
| 93 12219 | 6/1993 | WIPO . |

*Primary Examiner*—Jon P. Weber
*Assistant Examiner*—Deborah K. Ware
*Attorney, Agent, or Firm*—Pillsbury Madison & Sutro, LLP

[57] ABSTRACT

Filamentous microorganisms of improved properties, for example growth rate, may be obtained by culturing a sample of desired morphology until a substantial proportion of the culture diverges from that morphology, selecting an organism from the culture at that stage which exhibits the desired morphology and repeating the process with the selected microorganism. Furthermore, an isolated *Fusarium graminearum* having all of the characteristics of IMI 366464 and also possessing a greater morphological stability and growth rate than *Fusarium graminearium* strain IMI 145, 425 is disclosed.

11 Claims, 4 Drawing Sheets

MICROBIOLOGICAL PROCESS

This application claims benefit of international application PCT/GB95/00273, filed Feb. 10, 1995.

BACKGROUND OF THE INVENTION

THIS INVENTION relates to a microbiological process.

It is known how to grow filamentous microorganisms especially eukaryotic microorganisms, for example fungi in industrial processes, for example Aspergillus species, especially *Aspergillus oryzae* and *Aspergillus niger* are known for the production of citric acid; Penicillium species, especially Penicillium chrysogenum are known for the production of penicillin and Fusarium, especially *Fusarium graminearum* is grown for use in the manufacture of food.

It is desirable that the organisms should grow rapidly in the culture, as this increases the throughput per unit reactor volume.

In the culturing of such microorganisms hyphal branching occurs, and there may be a tendency for the population to become increasingly branched as culturing continues if the original microorganisms show little branching. This may present problems in the case of a product intended as food, leading to its having an unsatisfactory texture.

SUMMARY OF THE INVENTION

This invention comprises a method of modifying a filamentous microorganism which comprises culturing a sample of desired morphology until a substantial proportion of the culture population diverges from the desired morphology, selecting from the culture at that stage at least one microorganism exhibiting the desired morphology, and repeating said culturing with the selected microorganism at least once for example at least 3, and suitably at least 5 times.

It will be realised that the microorganisms of desired morphology are not identical and will diverge in size, and number or proportion of branching points.

Similarities in morphology are suitably judged in terms of numbers of filament ends per unit length of the total mycelium ie the hyphal growth unit length, though other criteria for assessing morphology may be used if desired.

It is believed that as the number of repeated culture and selection stages increases the selected microorganisms will increase in growth rate relative to their more normally branched variants and this will give them a selective advantage. Such an effect would allow an industrial process exhibiting unstable morphology to be continued longer thus increasing the availability of plant by reducing the proportionate amount of down-time and reducing the shut-down and start-up costs associated with operating plant over a period of time.

By "unstable morphology" is meant that on long continued culturing variants of undesired morphology eventually amount to an industrially unacceptable proportion of the total organisms present.

BRIEF DESCRIPTION OF THE DRAWINGS

FIG. 2(*a*) competition between A3/5 (closed symbols) and A21-XS (open symbols), FIG. 2(*b*) competition between A3/5 (closed symbols) and A23-S (open symbols), FIG. 2(*c*) competition between A3/5 (closed symbols) and A24-S (open symbols), FIG. 2(*d*) competition between A23-S (open symbols) and A24-S (closed symbols).

DETAILED DESCRIPTION OF THE INVENTION

Figure 1:
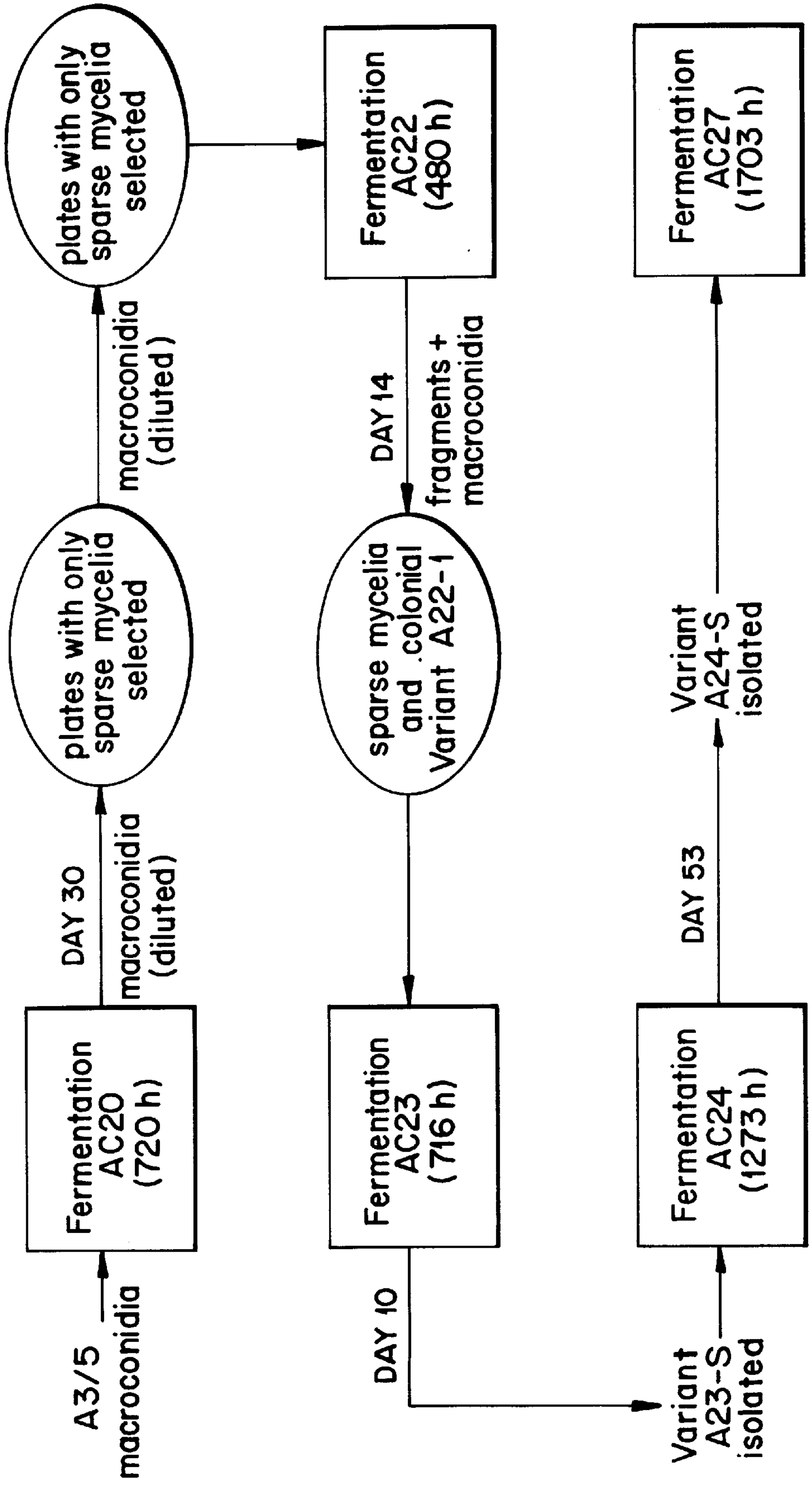
FIG. 1 Flow diagram showing the history of the chemostat cultures from which variants were isolated.

The invention is suitably carried out with Fusarium, for example *Fusarium solani* or *Fusarium oxysporium* but especially *Fusarium graminearum.* A food-approved sample of this organism is deposited with the Commonwealth Mycological Institute, (IMI) Ferry Lane, Kew, Richmond, Surrey England under deposit number CMI (formerly IMI) 145425 and with the American Type Culture Collection, 12301 Parklawn Drive Rockville, Md. 20852, USA under number ATCC 20334.

Suitable conditions of culture for this organism are disclosed for example in U.S. Plant Patent 4347, and European patent 123,434.

The successive cultures are conveniently carried out conventionally on a laboratory scale rather than on an industrial scale so as to have a culture which is pre-prepared according to the invention available for largescale use.

The invention also comprises a process of producing food which comprises the steps of fermenting a filamentous microorganism which is modified according to the invention and harvesting the organism.

The harvested organism may be treated to reduce its nucleic acid content by the process of UK Patent 1,440,642, separated if desired by the procedure of UK Patent 1,473, 654 or by filtration or centrifugation, and its palatability modified for example by the procedures of UK Patents 1,508,635, 1,502,455, 1,496,113 and/or 1,587,828. To be successful as human food the proteinaceous products must have an acceptable texture, particularly a so-called "mouth feel" which may correspond to that of meat or fish to be simulated. A difficulty in this respect is that the structure of the proteinaceous composition is dependent on the structure of the filamentous microorganisms of which it is composed, and that the structure of such filamentous microorganisms should therefore be similar to that of the meat to be simulated. It is important, therefore to be able to control the structure of the filamentous microorganism, in particular the extent of branching occurring in the hyphae. A useful indicator of the extent of branching is the "hyphal growth unit length". This may be determined by dividing the total length of all filaments of a mycelium by the total number of hyphal tips in the mycelium. In general organisms which show low branching are preferred for this purpose.

The desired morphology in the case of a filamentous microorganism used as a food will normally be one in which there is little branching; for example the average number of filament ends per millimetre may be 1.5 to 5 for example 2 to 4. Microorganisms diverging from the desired morphology have more than 5 filament ends per millimetre.

The invention also comprises a process for the production of a proteinaceous composition from a filamentous microorganism of the genus Fusarium which process comprises preparing Fusarium by selection for a desired morphology by a process according to the invention, and cultivating the selected Fusarium under aerobic conditions in a culture medium containing a carbon source and sources of other essential nutrients.

Cultivation may be conducted in chemostat culture or turbidostat culture. In order that improved productivity may be obtained it is preferred, however, that the cultivation is conducted in a turbidostat culture, i.e. one in which the concentration of organisms in the culture is held within desired limits. This concentration produces a turbidity within corresponding limits. The majority of microbial cells present are not subjected to any specific nutrient limitation. When cultivation is conducted in turbidostat culture the concentration of the microbial cells within the fermenter may be controlled within desired limits by the rate at which nutrient medium is added and culture removed (the "dilution rate") but if desired this effect may be reinforced by varying the temperature or composition of the nutrient medium. It is, of course not necessary that the turbidity of the culture should be measured or monitored as it may be more convenient to monitor another related parameter instead for example $CO_2$ evolution.

Cultivation may be conducted batchwise, or continuously. Preferably, the cultivation is continuous.

The temperature at which the process is conducted may be selected according to the particular microorganism under cultivation so as to produce acceptable yields and substrate, especially carbon source conversion ratios. Typical temperatures are within the range 25 to 34° C.

Similarly, the pH at which the process is conducted is preferably kept within a range at which maximum growth is exhibited for a particular microorganism. Typically the pH is within the range 5.0 and 8.0, and more usually about a pH of 6.

In the culture medium the carbon source may be any suitable carbon source, for example starch, starch containing materials, or products of their hydrolysis, e.g. glucose, sucrose, sucrose containing materials or hydrolysed sucrose, i.e. invert sugars, or mixtures thereof. Thus the carbon source may comprise hydrolysed potato, molasses, glucose, matrose, hydrolysed bean starch or cassava. Alternative carbon sources, such as carbon sources of animal origin e.g. milk whey, may also be used. Sufficient amounts of an assimilable carbon source together with other essential growth elements such as nitrogen, sulphur, phosphorus and trace elements are maintained in the culture medium so that growth of the microorganism is not limited by any of these nutrients. The dissolved oxygen tension (DOT) is maintained at a sufficient level and is preferably at a level at which no substantial part of the culture is in oxygen limitation. In addition to the nutrients discussed above the presence of one or more vitamins such as biotin may be included in the culture medium.

During the process, culture medium is preferably continuously supplied to the culture and culture is continuously removed from the fermenter. The removed culture may then be treated to separate the filamentous microorganism therefrom. In a typical treatment the removed culture is heat treated, separated from its growth medium for example by filtration and then formulated into a state suitable for use in food products.

Where culture medium is continuously supplied to, and culture is continuously removed from the fermenter, the total number of individual mycelia in the fermenter is determined by the generation of new hyphal fragments (starter cells) through conidation and cell breakage. During cultivation it is important that starter cells are continuously produced in the culture. Ideally these starter cells should be generated at approximately the same rate at which the cells are removed from the culture. If no starter cells are produced there will of course be a "wash-out" of the culture.

Suitable strains of Fusarium include *Fusarium graminearum* Schwabe. Strains IMI 145425 deposited Feb. 26, 1970, and 154209 to 154213, deposited Jan. 14, 1971, (all of which became publicly available on Feb. 3, 1976) or variants, or mutants of these strains are particularly suitable. These specific strains of *Fusarium graminearum* are described in GB 1346061, the disclosure of which is incorporated herein by reference, and are deposited at the CAB International Mycological Institute, (IMI), Ferry Lane, Kew, Richmond, Surrey, England. Strain 145425 is also deposited under the Budapest Treaty as IMI 346762 and also ATCC 20334 at the American Type Culture Collection, 12301 Parklawn Drive, Rockville, Md. 20852, USA.

We have found that the invention may be carried out with surprising effectiveness if the initial culturing of the organism is carried out by turbidostat culturing. It is desirable to continue such culturing to a stage at which the culture comprises mainly, for example at least 50% and preferably at least 80% and more preferably at least 90% of variants of undesired morphology before selecting from it variants of desired morphology. Preferably this stage is carried out on a laboratory scale as the product as a whole is likely to be commercially valueless.

The invention comprises an edible strain of *Fusarium graminearum* produced by cultivating an edible strain of Fusarium having an average of at most 5 for example 1.5 to 5 and preferably at most 4 filament ends per millimetre of its total length (including the length of all hyphae) under turbidostat conditions until at least 80% and preferably at least 90% of the organisms present have more than 5 filament ends per millimetre, and selecting an organism having an average of at most 4 filament ends per millimetre therefrom.

The invention also comprises *Fusarium graminearum* strain ES1, deposited at the International Mycological Institute, Bakeham Lane, Egham, Surrey TW20 9TY, England under deposit number IMI 366464 on Feb. 3, 1995.

The invention is illustrated by the following Examples.

EXAMPLE 1

Organism and Medium

*Fusarium graminearum* Schwabe strain A3/5, IMI 145425 was maintained as macroconidia at −70° C. in 20% (v/v) glycerol. Macroconidia for inocula were prepared as described in Wiebe et al, Mycological Research 95 1284–1288 (1991) (Ref 1).

The medium described by Vogel, Microbial Genetics Bulletin 13 42–44 (1956) was used with glucose as the carbon source instead of sucrose. 1.65 g $(NH_4)_2SO_4l^{-1}$ was substituted for 2.0 g $NH_4NO_3l^{-1}$ as the nitrogen source. Vogel's mineral salts solution was prepared at 50× final concentration, sterilised by membrane (0.2 μm diam pore size) filtration and added to the sterile glucose solution. Glucose solutions (final concentration of 3.0 g glucose $1^{-1}$ medium) for chemostat cultures were prepared in 10 1 volumes and autoclaved for 60 min at 121° C.; no caramelization and no significant loss of glucose was observed. For Plate cultures, Vogel's modified medium containing 10.0 g glucose $l^{-1}$ and 3 g $(NH_4)_2SO_4l^{-1}$ or 2 g $NH_4NO_3l^{-1}$ or 2 g $NaNO_3l^{-1}$ was solidified with agar (Davis Gelatine; 15 g $l^{-1}$, final concentration). For media to detect resistant strains, cycloheximide (250 $\mu$M) or potassium chlorate (300 mM) was added to modified Vogel's medium. All cultures were incubated at 25° C.

Chemostat Cultures

Cultures were grown in a Braun (B. Braun Medical Limited, Aylesbury, Bucks) Biostat M(2 1) fermenter as described by Wiebe & Trinci Biotechnology and Bioengineering 38, 75–81 (1991). Biomass retention in the fermenter vessel was monitored daily by taking dry weight measurements of samples both from inside the fermenter vessel and from the overflow. No retention of biomass in the vessel was observed.

Isolation of Variants

A sample was taken from the first chemostat (AC20) after 720 h (196 generations) of cultivation and macroconidia (separated from the mycelial biomass by filtration through lens tissue) from this sample were diluted and used to inoculate agar-solified modified Vogel's plates. Only plates which contained no colonial variant colonies were retained and used to harvest macroconidia to inoculate fresh plates (to ensure that no colonial variants were present in the final inoculum). This second set of plates was used to produce macroconidia to inoculate a second chemostat (AC22) in the series. 312 h (89 generations) after the onset of continuous flow, samples (using a suspension containing mycelia and conidia) from AC22 were used to inoculate a fresh glucose-limited chemostat (AC23). Variant A23-S was isolated from the AC23 chemostat at 240 h after the onset of continuous flow (total time since inoculation of the chemostat series with A3/5 was 1248 h or 336 generations); a highly branched, colonial variant (A22-1) was present in the fermenter population at a very low concentration at this time. Variant A24-S was isolated from the AC24 chemostat which had been inoculated with macroconidia of A23-S (FIG. 1). This culture was maintained for 1273 h (total time since inoculation of the chemostat series with A3/5 was 2482 h or 658 generations). The history of these cultures is shown in FIG. 1. Variant A21-XS was isolated from a similar of glucose-limited chemostats initially inoculated with *F. graminearum* A3/5.

Marking Variants for Competition Experiments

Chlorate-resistant variants of strains A3/5, A23-S, A24-S and A21-XS were generated by inoculating plates of modified Vogel's medium containing 300 mM potassium chlorate with ca. 5×104 macroconidia and subsequently isolating chlorate-resistant colonies. Each isolate was subcultured onto plates of Vogel's medium containing $NaNO_3$ as the sole nitrogen source, as well as onto Vogel's medium containing $NH_4NO_3$. Only nitrate-non-utilising strains were retained for the experiments described below.

Monitoring of Cycloheximide-Resistant Variants and Morphological (Colonial) Variants Samples (ca 10 ml) were removed daily from the fermenter vessel and cycloheximide resistance in the macroconidial population was monitored. Macroconidia were separated from the mycelial biomass by filtering the sample through two layers of sterile lens tissue and counts of viable macroconidia were made on modified Vogel's medium (10 replicates per sample), as described by Ref 1. Macroconidia (ca 3×104 per plate) were also inoculated onto medium containing 250 $\mu$M cycloheximide (10 replicates per sample). The plates were incubated at 25° C. for 3 days for viable counts, or 6–8 days to detect cycloheximide resistance.

Highly branched, morphological variants were identified from their colonial morphologies Trinci Mycological Research 96 1–13 (1992) and the proportion of colonial variant(s) to parental strain was determined in the total population (i.e. macroconidia and mycelial fragments) as described by Ref 1.

Measurement of Selection Coefficients

Selection coefficients, as defined by Dykhuizen & Hartl Evolution 35 581–594 (1981) were calculated for cultures inoculated with macroconidia of two different strains. Morphologically similar strains were distinguished by competing chlorate-resistant (nitrate-non-utilising) and chlorate-sensitive (nitrate-utilising) strains. Counts of colony forming units (derived from either mycelial fragments or macroconidia) were made on modified Vogel's medium containing $NH_4NO_3$ or $NaNO_3$ as the nitrogen source, and with $NH_4NO_3$ plus 300 mM chlorate (20 replicates per sample for each medium). The plates were incubated for 3 days and the proportion of chlorate-resistant and chlorate-sensitive propagules in the total population was determined. Each competition was repeated with the chlorate-resistance marking the other strain. To calculate selection coefficients for the colonial strain A22-1, it was not necessary to use chlorate-resistant strains, as highly branched variants are easily distinguishable from sparsely branched strains.

Measurements of Colony Growth and Mycelial Morphology

Petri dishes (9 cm diam) containing 20 ml Vogel's modified medium were inoculated centrally with small volume of a suspension of macroconidia. Measurements of colony diameters were made with a rule at magnifications of ×10 using a Shadowmaster (Baty & Co., Burgess Hill, Sussex) as described by Trinci J. General Microbiology 57 11–24 (1969).

Hyphal growth unit (G) length is a measure of mycelia branching and these measurements were made on mycelia which had been grown for ca 24 h in liquid medium; submerged cultures were grown in 50 ml volumes of medium in 250 ml Ehrlenmeyer flasks, incubated on a rotary shaker (with a throw of 2.5 cm) at 200 r.p.m. Hyphal growth unit lengths were measured using a MeasureMouse system (Analytical Measuring System) and a Nikon Microscope linked to a videocamera and an Amstrad 1512PC computer.

RESULTS

Morphology of A21-XS, A23-S and A24-S

Variant A21-XS is significantly more sparsely branched (longer G value) than the parental strain whilst, as shown in Table 1, A23-S and A24-S had mycelial morphologies (G values) which were not significantly different from the parental strain (A3/5). The colony radial growth rates of strains A3/5, A23-S and A24-S were also not significantly different.

Competition Between the Parental Strain A3/5 and A21-XS

Figure 2A:
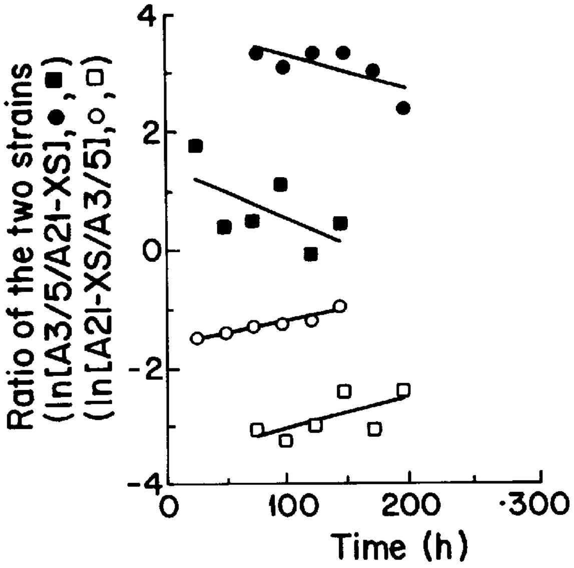
FIG. 2 Competitions between chlorate-resistant ( , ) and chlorate-sensitive ( , ) strains of *F. Graminearum* grown in glucose-limited chemostat culture at a dilution rate of 0.18 $h^{-1}$.

When grown in glucose-limited chemostat culture at a dilution rate of 0.18 $h^{-1}$, A21-XS had a selection coefficient of 0.006±0.001 $h^{-1}$ relative to the parental strain (A3/5) (FIG. 2*a*).

Competition Between A3/5, A23-S and A24-S

Figure 2B:
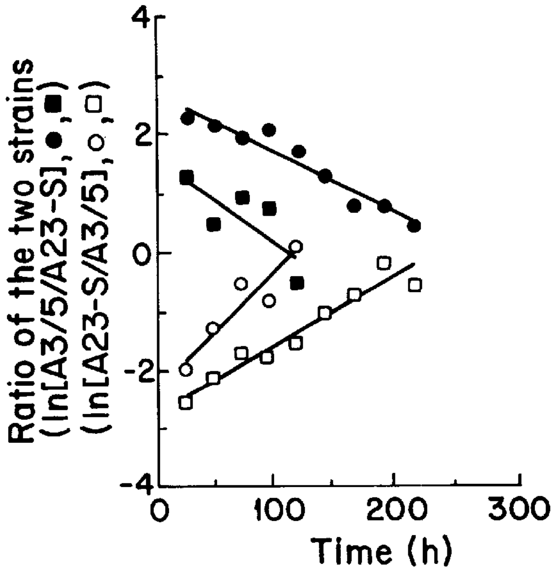
Figure 2C:
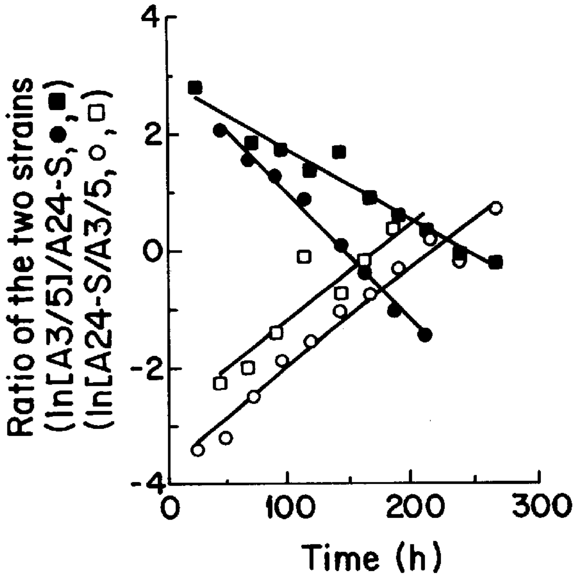
Figure 2D:
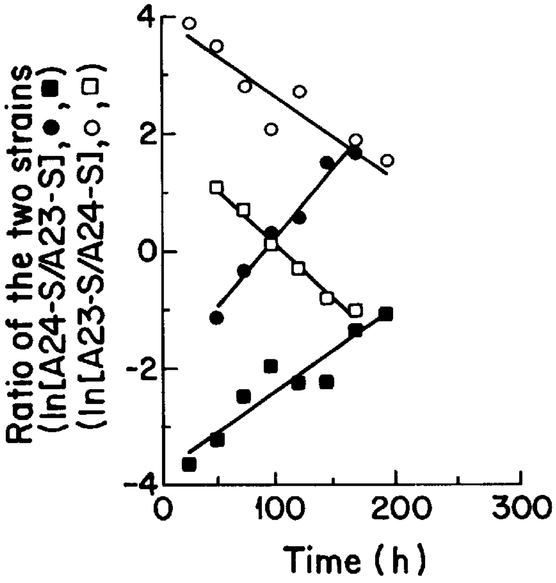

The parental strain (A3/5) was grown in mixed culture with the morphologically unaltered variants A23-S and A24-S. When grown in mixed culture in a glucose-limited chemostat culture at a dilution rate of 0.18 $h\text{-}^{-1}$, A23-S replaced A3/5 (FIG. 2*b*) with a selection coefficient of 0.013±0.001 $h^{-1}$. Similarly, when mixed cultures of A24-S and A3/5 were grown under the same conditions, A24-S replaced A3/5 (FIG. 2*c*) with a selection coefficient of 0.017±0.002 $h^{-1}$; the selective advantage of A24-S relative to A3/5 was significantly greater ($p<0.10$, t-test) than the selective advantage of A23-S relative to A3/5. When morphologically unaltered variants A23-S and A24-S were grown in glucose-limited chemostat culture at a dilution rate of 0.18 $h^{-1}$, A24-S replaced A23-S (FIG. 2*d*) with a selection coefficient of 0.014 $h^{-1}$.

Competition Between A3/5, A22-1 and A23-S

Figure 3:
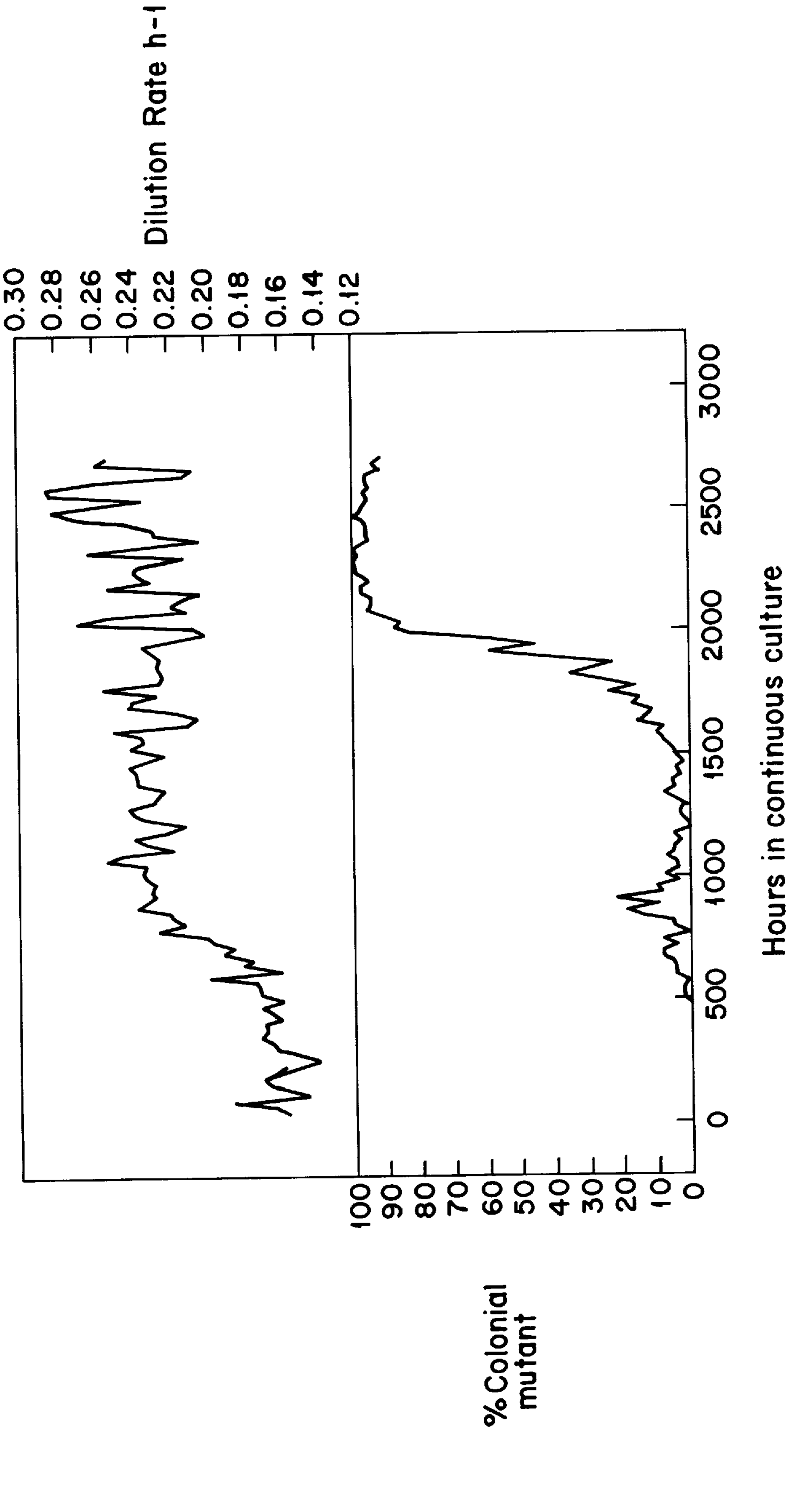
FIG. 3 Time-course trends for dilution rate and the proportion of colonial variants observed during continuous culture.
Figure 4:
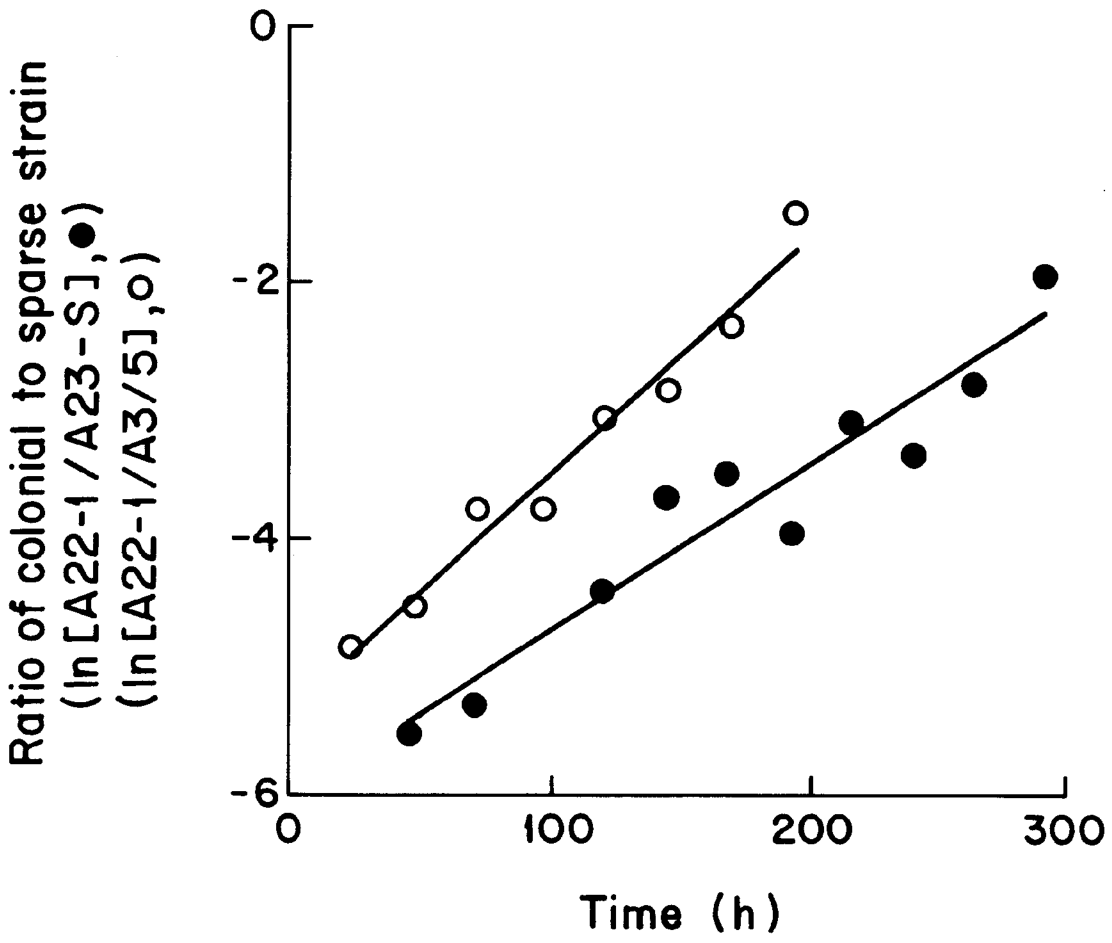
FIG. 4 Competitions between *F. Graminearum* A3/5 and colonial variants A22-1 (o) and between A23-S and colonial mutant A22-1 ( ) grown in glucose limited chemostat culture at a dilution rate of 0.18 $h^{-1}$.

The parental strain (A3/5) and A23-S were each grown (separately) in competition with A22-1 (a highly branched variant) in glucose-limited chemostat culture at a dilution rate of 0.18 $h^{-1}$. FIG. 3 shows that the highly branched (colonial) variant supplanted both sparsely branched strains but the parental strain (A3/5) was displaced more rapidly ($s=0.019\ h^{-1}$) than the A23-S variant ($s=0.013\ h^{-1}$).

Appearance of Colonial Variants and Periodic Selection in a Chemostat Culture of Variant A23-S A monoculture of variant A23-S was grown in glucose-limited chemostat culture at a dilution rate of 0.18 $h^{-1}$. Highly branched (colonial) variants appeared in the population after 480 h (ca 124 generations) and replaced A23-S with a selection coefficient of 0.018 $h^{-1}$. Although the majority of the colonial population consisted of very highly branched variants less highly branched variants were occasionally observed but never formed more than 1.4 ±0.9% of the population. After 937 h (ca 245 generations), highly branched (colonial) variants formed 84±1.6% of the population and then fluctuated between 80 and 90% of the total population until the experiment was terminated at 1273 h (ca 334 generations).

Fluctuations occurred in the concentration of cycloheximide resistant macroconidia in the population and seven peaks of cycloheximide resistance were observed (Table 2). Excluding the interval before the first peak in the cyclohyximide resistant population (384 h), an average interval of 160±12 h (42±3 generations) was observed between peaks. Cycloheximide resistant colonial variants were first observed after 601 h (ca 156 generations), but they did not become dominant in the cycloheximide resistant population until 816 h (ca 213 generations, peak 4). Fluctuations continued to be observed in both the cycloheximide resistant A23-S and colonial variant populations (Table 2).

Appearance of Colonial Variant and Periodic Selection in a Chemostat Culture of A24-S)

A monoculture of A24-S was grown in glucose-limited chemostat culture at a dilution rate of 0.18 $h^{-1}$. Highly branched (colonial) variants appeared in the population after ca 600 h (ca 156 generations) after the onset of continuous medium flow, and displaced the sparsely branched population with a selection coefficient of 0.023 $h^{-1}$. In a second experiment, no colonial variants were observed in the A24-S population in the chemostat after 552 h of continuous flow when the fermentation was terminated. After 912 h (ca 237 generations) of cultivation, the colonial population contributed 85.2±3.2% of the total population and subsequently fluctuated between this and 96.4±0.8% of the population until the fermentation was terminated at 1703 h (ca 442 generations).

Fluctuations in the concentration of cycloheximide resistant macroconidia were also monitored during this experiment and seven peaks of cycloheximide were observed (data not shown). After the first interval, which lasted ca. 336 h, the average interval between peaks was 208±28 h (ca 54 generations) which was significantly ($p<0.10$, t-test) longer than for either A3/5 or the A23-S (Table 2) chemostat populations.

Thus advantageous variant of *F. graminearum* A3/5 with three different morphologies have now been isolated.

i variant more highly branched than A3/5 (the colonial variant);

ii variants with similar branching patterns to A3/5 (A23-S and A24-S); and iii variants more sparsely branched than A3/5 (A21-XS).

Colonial variants appear in chemostat-grown populations of *F. graminearum* after ca. 390 h and their selection coefficients relative to the parental strain (A3/5) vary from 0.017 to 0.034 $h^{-1}$. Thus, compared with the sparsely branched advantageous variants (A21-XS, A23-S and A24-S) reported here, colonial variants appear in glucose-limited cultures of A3/5 more rapidly and have higher selection coefficients.

Variant A23-S was grown in glucose-limited chemostat culture to determine both the frequency of adaptive peaks and the time when colonial variants first appeared. The interval before the first peak was longer (384 h) than the first interval (longest interval=171 h) observed for chemostat populations of the parental strain (A3/5), suggesting that the former culture was more homogenous at the onset of continuous medium flow than the latter. A similarly long first interval (336 h before the first peak in cycloheximide resistance) was observed for both A24-S fermentations. Excluding this first interval, an average interval of 160±12 h (42±3 generations) was observed between peaks in cycloheximide resistance for the A23-S culture. This is significantly longer ($p<0.05$) than the average interval between peaks in cycloheximide resistance in A3/5 cultures (124±12 h) suggesting that, although changes in the population continue to occur, they occur less frequently than in the A3/5 populations. The average interval between peaks in cycloheximide resistance for a glucose-limited chemostat culture of A24-S (208±28 h) was greater ($p<0.10$) than the interval (160±12 h) observed for the A23-S culture.

TABLE 1

Hyphal Growth Unit Lengths and Colony Radial Growth Rates of *F. Graminearum* A3/5, A23-S and A24-S in Solid and Submerged Culture

*F Graminearum* A3/5, A23-S and A24-S were grown on modified Vogel's medium with or ammonium sulphate as the nitrogen source at 25° C. The results are the means (± standard error) of 6* and 25# replicates respectively. Figures in the same column, and on the same nitrogen source, with the same superscript letter are not significantly different ($P > 0.05$).

| Strain | Hyphal Growth Unit Length in Liquid Medium (G, $\mu$m) # | Colony Radial Growth rate ($K^r$ $\mu$m $h^{-1}$)* |
|---|---|---|
| Parental strain (A3/5) | $224 \pm 10^a$ | $101 \pm 3^a$ |
| A23-S | $190 \pm 5^a$ | $100 \pm 4^a$ |
| A24-S | $201 \pm 10^a$ | $125 \pm 5^b$ |

TABLE 2

Periods between Peaks in the Proportion of Cycloheximide Resistant Macroconidia in a Population of *F. graminearum* A23-S

*F. Graminearum* A23-5 was grown in glucose-limited (3 g glucose $l^{-1}$ medium) chemostat culture on modified Vogel's medium (25° C., pH 5.8 ± 0.1) at a dilution rate of 0.18 $h^{-1}$. Samples were removed at regular intervals and the proportion of cycloheximide (0.25 mM) resistant macroconidia in the total macroconidial population was determined. This proportion was also determined for two subpopulations (sparsely-branched or and highly branched phenotypes).

| | Time between peak maxima (h) | | | | | | |
|---|---|---|---|---|---|---|---|
| Population | Peak 0-1 | Peak 1-2 | Peak 2-3 | Peak 3-4 | Peak 4-5 | Peak 5-6 | Peak 6-7 |
| Total Population | 384 | 191 | 145 | 144 | 168 | 120 | 192 |
| Sparsely-branched mutant sub-population | 384 | 191 | 145 | 144 | 168 | 96 | 216 |
| Highly branched mutant sub-population | | | | | 216 | 96 | 192 |

EXAMPLE 2

Organism and Medium

*Fusarium graminearum* Schwabe strain A3/5 (IMI 145425) was maintained as hyphal fragments suspended in 10% (v/v) glycerol and stored in vials (2 ml) held at −196° C. Seed cultures for fermentation experiments were prepared by transferring all or part of the contents of one of these vials to one liter Ehrlenmeyer flasks containing 250 ml of RHM growth medium. Cultures were developed by incubating at 28° C. for up to 72 h. The composition of RHM medium is as follows:

| Component | per 1 |
|---|---|
| D-Glucose | 10.0 g |
| $K_2SO_4$ | 0.3 g |
| $NH_4Cl$ | 4.4 g |
| $MgSO_4.7H_2O$ | 0.25 g |
| $KH_2PO_4$ | 10.0 g |
| Biotin solution[A] | 1.0 ml |
| Trace elements solution[B] | 5.0 ml |

[A]Biotin solution: 30 mg $l^{-1}$ biotin (Sigma Chemical Co., Poole, UK)
[B]Trace elements solution:

| Component | per 1 |
|---|---|
| $CaCl_2.2H_2O$ | 2.0 g |
| $FeCl_3.6H_2O$ | 2.0 g |
| Citric Acid | 1.5 g |
| $ZnCl_2$ | 1.0 g |
| $MnCl_2.4H_2O$ | 1.0 g |
| $CuCl_2.2H_2O$ | 0.2 g |
| $CoCl_2.2H_2O$ | 0.2 g |
| $NaMoO_4.2H_2O$ | 0.2 g |

All components except biotin were dissolved collectively in de-ionised water and the solution sterilised by autoclaving at 121° C. for 20 min. Biotin was prepared separately as a filter sterilised solution which was added to the other the medium components after autoclaving and cooling.

Turbidostat Cultures

Cultures were grown in a Braun (B. Braun Biotech, Aylesbury, Bucks) Biostat S type fermenter with a working volume of 3.2 liters. The imposed set points were: temperature 28° C.; pH 6.0 (maintained by autotitration of 7 M $NH_4OH$); agitation 1000 rpm; air flow rate 2.51 $min^{-1}$. Foaming was suppressed by the timed addition of polypropylene glycol antifoam oil at a rate of 0.1–0.2 ml $h^{-1}$.

Two independent feed streams (in addition to $NH_4OH$ and polypropylene glycol) delivered nutrient solutions which collectively formed the growth medium:

1 Iron was supplied from a solution containing 0.5 g $l^{-1}$ $FeSO_4.7H_2O$ acidified with 0.5 ml $l^{-1}$ of concentrated $H_2SO_4$. This was sterilised by autoclaving at 121° C. for 30 min.

2 Minimal salts supplemented with glucose as the carbon and energy source was prepared by mixing together equal volumes of two aqueous solutions which were prepared independently and sterilised by autoclaving at 121° C. for 30 min. The components were as follows:

a) $K_2SO_4$, 4 g $l^{-1}$; $MgSO_4.7H_2O$, 1.8 $gl^{-1}$; $Ca(CH_3.COO)_2$, 0.4 $gl^{-1}$; $H_3PO_4$ (85%) 2.3 ml $l^{-1}$; $ZnSO_4.7H_2O$, 50.0 mg $l^{-1}$; $MnSO_4.4H_2O$, 40.0 mg $l^{-1}$; $CuSO_4.5H_2O$, 5.0 mg $l^{-1}$; Biotin, 50.0 $\mu$g $l^{-1}$.

b) 66 g $l^{-1}$ glucose monohydrate (Meritose granules ex Tunnel Refineries).

The fermenter vessel was filled with minimal salts + glucose solution then supplemented with iron sulphate to give a final $Fe^{2+}$ concentration of 1 mg $l^{-1}$ in the growth medium. Control set points were established and the inoculum culture introduced. Growth was monitored by on-line analysis of the off-gas composition by mass spectrometry which was used to calculate rates of carbon dioxide evolution (CER). Continuous-flow culture was established by switching on pumps delivering antifoam, iron and minimal salts + glucose when the CER had reached 27 m mol $l^{-1}$ $h^{-1}$. Iron was added at a fixed rate equivalent to an $Fe^{2+}$ concentration of 0.8–1.0 mg $l^{-1}$ in the inflowing growth medium.

A feedback loop incorporating CER as the central controlled variable was used to regulate the flow rate of the minimal salts + glucose stream during continuous-flow. Signals received from the mass spectrometer were processed by software which was programmed to generate one of two output voltages in response to changes above or below the CER set point of 48 m mol $l^{-1}$ $h^{-1}$. The output voltage controlled the rotational speed of a peristaltic pump delivering the minimal salts + glucose stream and therefore the dilution rate since this stream alone accounted for over 95% of the total liquid flow passing into the fermenter. In practice the two output voltages corresponded to dilution rates of approximately 0.15 and 0.25 $h^{-1}$. These were designed to either further concentrate or dilute the biomass respectively. Regulated switching between the two limits was carried out under supervision by the software and the equilibrium maintained at a value which corresponded to the organism's maximum growth rate. This method of operation enabled excess levels of glucose to be maintained in the culture broth whilst operating at the maximum permissible dilution rate.

Monitoring of Colonial Morphology

Samples of fresh culture (ca 10 ml) were removed daily from the fermenter and diluted serially in sterile Ringers solution. Aliquots (0.1 ml) of the appropriate dilutions were spread onto the surface of 10 agar plates containing solidified malt extract medium. These were incubated at 28° C. for up to 48 h. Highly branched, morphological variants were identified by their colonial morphologies and the proportion of colonial variants to parental strain in the total population determined as described in Example 1.

Measurements of Mycelial Morphology

Measurements were made of the hyphal growth unit (G) length on mycelia which had been grown for up to 48 h. The cultures were grown in 50 ml of RHM medium contained in 250 ml Ehrlenmeyer flasks which were incubated at 28° C. on a New Brunswick 25G orbital shaker set at 150 rpm. Measurements on 25 fragments having 5 tips or more were carried out using a computerised image analyser (Kontron Image Processing System). This received images from a videocamera mounted on an Olympus BH2 microscope.

RESULTS

Cultures Evolution and Isolation of Variant ES1

*Fusarium graminearum* strain A3/5 was established in turbidostat culture which was concluded after an elapsed operating period of 1943 h. Samples taken throughout this period were used to prepare stock cultures which were stored subsequently in liquid nitrogen at 196° C. A stock culture which had been laid down at 1820 h was used to inoculate a second fermentation which was carried out using the same operating protocol as had been applied to the first. Samples removed during this second fermentation, which was concluded after 808 h, were also used to prepare stock cultures. Thus far no attempt had been made to isolate individual variants from the population during the total cultivation period represented by the two fermentations.

FIG. 3 gives time-course trends for dilution rate and the proportion of colonial variants observed in the population during the combined evolutionary period of 2628 h. Data collected during continuous-flow of both fermentations are joined (the batch phase of the second fermentation has been left out to simplify interpretation). The imposed operating conditions were successful in selecting variants with a higher maximum specific growth rate since an increase in dilution rate from around 0.16 $h^{-1}$ to values typically in excess of 0.2 $h^{-1}$ was required to maintain CER at 48 m mol $l^{-1}$ $h^{-1}$. Variants with highly branched colonial morphology were also positively selected and ultimately these became dominant. However a limited number of colonies bearing the sparsely branched parental morphology could still be detected; one such colony, from a sample taken at the conclusion of the second fermentation was isolated and given the strain code ES1. It was deposited with International Mycological Institute, Bakeham Lane, Egham, as IMI 366464 under the terms of the Budapest Treaty on Feb. 3, 1995.

Morphology of ES1

The mycelial morphology of ES1 in submerged liquid culture was not significantly different to that of A3/5. Hyphal growth unit lengths of 328±63 and 297±49 μm respectively were recorded for the two strains.

Dilution Rate and Appearance of Colonial Variants in a Turbidostat Culture of Variant ES1

A monoculture of variant ES1 was grown in turbidostat culture and daily measurements made of the mean dilution rate. Colonial morphology was also monitored to establish the point at which colonial mutants were first detected within the population. The following table compares the results with those obtained when the parental strain (A3/5) was grown under similar conditions.

TABLE 3

| Parameter | Strain A3/5 | Strain ES1 |
|---|---|---|
| Mean dilution rate ($h^{-1}$) | 0.161 ± 0.010 (20) | 0.207 ± 0.016 (24) |
| Mean generation time (h) | 4.3 | 3.4 |
| Time of first detection of highly branched variants (h) | 494 | 573 |
| Time of first detection of highly branched variants (generations) | 115 | 171 |

An average increase of 34% in the maximum operating dilution rate was observed when ES1 was used as the process strain. In addition the appearance of highly branched colonial mutants was delayed by a period equivalent to 56 generations. These combined effects suggest that ES1 has the potential to produce approximately 50% more biomass than A3/5 during the course of a fermentation before highly branched variants are observed. This is based on the assumption that both are operating on an equivalent biomass basis.

We claim:

1. A process of modifying a filamentous microorganism to increase its growth rate and morphological stability which comprises selecting a filamentous microorganism having a morphology as represented by hyphal growth unit length, culturing a sample of the selected filamentous microorganism having said morphology to obtain a culture population in which at least 50% of the culture population differs from said morphology, selecting from the culture population at least one microorganism exhibiting said morphology, and repeating said culturing with the microorganism selected from said cell population at least once until modified filamentous microorganism having increased growth rate and morphological stability is obtained.

2. The process according to claim 1 in which the culturing is repeated at least three times, each time selecting a micro-organism having said morphology for culturing in the successive stage.

3. The process as claimed in claim 1 in which the filamentous micro-organism is of the genus Fusarium.

4. The process as claimed in claim 3 in which the modified microorganism has 1.5 to 5 filament ends per millimetre and in which microorganisms diverging from the culture population have more than 5 filament ends per millimetre.

5. The process according to claim 1 which comprises producing a modified edible strain, of Fusarium by cultivating an edible strain of Fusarium having an average of 1.5 to most 5 filament ends per millimetre of its total length including the length of all hyphae under turbidostat conditions until at least 80% of the microorganisms present have more than 5 filament ends per millimetre, and selecting a microorganism having an average of 1.5 to 4 filament ends per millimetre therefrom for further culturing.

6. A process of producing human food which comprises cultivating a filamentous micro-organism modified according to claim 1 and harvesting it.

7. The process according to claim 1 wherein the filamentous microorganism exhibiting the morphology is selected on the basis of minimum branching as defined by a hyphal growth unit length such that the average number of filament ends per millimetre of cultured filamentous microorganism is 1.5 to 4, the selection and culturing of said filamentous microorganism being continued to increase the growth rate thereof relative to more branched variants of said filamentous microorganism.

8. The process according to claim 1 wherein the morphology of the selected filamentous microorganism comprises branching of an average number of filament ends per millimetre of 1.5 to 5; and the culturing comprises turbidostat culturing and is continued until at least 50% of the culture population has more branching than the next selection of filamentous microorganism having the morphology and further culturing thereof is carried out.

9. A micro-organism which has been modified by a process according to claim 1.

10. A human food which comprises a micro-organism according to claim 9, which has been further processed to reduce its nucleic acid content.

11. An isolated *Fusarium graminearum* possessing all of the characteristics of strain ES1 deposited under deposit number IMI 366464 and strains of *Fusarium graminearum* derived therefrom, said strains having a morphological stability and growth rate greater than *Fusarium graminearum* strain A 3/5 deposited under deposit number IMI 145,425.

* * * * *